United States Patent
Liu et al.

(10) Patent No.: US 10,499,867 B2
(45) Date of Patent: Dec. 10, 2019

(54) METHOD, STORAGE MEDIUM, AND SYSTEM FOR ANALYZING IMAGE SEQUENCES OF PERIODIC PHYSIOLOGICAL ACTIVITIES

(71) Applicant: Shenzhen Keya Medical Technology Corporation, Shenzhen (CN)

(72) Inventors: Xiaoxiao Liu, Bellevue, WA (US); Shubao Liu, College Park, MD (US); Bin Ma, Bellevue, WA (US); Kunlin Cao, Kenmore, WA (US); Youbing Yin, Kenmore, WA (US); Yuwei Li, Bellevue, WA (US); Qian Zhao, GuiLin (CN); Qi Song, Seattle, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 159 days.

(21) Appl. No.: 15/864,398

(22) Filed: Jan. 8, 2018

(65) Prior Publication Data
US 2019/0209113 A1   Jul. 11, 2019

(51) Int. Cl.
*A61B 6/00* (2006.01)
*G06T 7/20* (2017.01)
*G06F 16/50* (2019.01)

(52) U.S. Cl.
CPC .............. *A61B 6/504* (2013.01); *G06T 7/20* (2013.01); *G06F 16/50* (2019.01); *G06T 2207/30004* (2013.01)

(58) Field of Classification Search
CPC ...... H04N 19/527; H04N 19/17; H04N 19/51; H04N 7/0157; G06T 2207/10016; G06T 7/20; A61B 5/055; A61B 6/504
See application file for complete search history.

(56) References Cited

U.S. PATENT DOCUMENTS 7,043,063 B1 * 5/2006 Noble ................... G06T 7/0016
                                                      382/107
10,229,504 B2 * 3/2019 Bigioi ................ H04N 5/23229
(Continued)

OTHER PUBLICATIONS

María J. Ledesma-Carbayo et al., "Spatio-Temporal Nonrigid Registration for Ultrasound Cardiac Motion Estimation," *IEEE Transactions on Medical Imaging*, vol. 24, No. 9 (Sep. 2005), pp. 1113-1126.

(Continued)

*Primary Examiner* — Jingge Wu
(74) *Attorney, Agent, or Firm* — Bayes PLLC (57) ABSTRACT

The present disclosure relates to a method, storage medium, and system for analyzing an image sequence of a periodic physiological activity. In one implementation, the method includes receiving the image sequence acquired by an imaging device, the image sequence having a plurality of frames and determining local motions for pixels in each frame of the image sequence. The local motion for a pixel may be determined using corresponding pixels in frames adjacent to the frame to which the pixel belongs. The method further includes determining principal motions for the plurality of frames based on the local motions; determining a motion magnitude profile based on the principal motions; and determining the phase of each frame in the image sequence based on the motion magnitude profile.

14 Claims, 4 Drawing Sheets

(56) References Cited

U.S. PATENT DOCUMENTS

| | | | |
|---|---|---|---|
| 2005/0107704 A1* | 5/2005 | Von Behren | A61B 5/0456 600/443 |
| 2005/0215904 A1* | 9/2005 | Sumanaweera | A61B 8/14 600/458 |
| 2008/0051660 A1* | 2/2008 | Kakadaris | A61B 8/06 600/454 |
| 2008/0095417 A1* | 4/2008 | Pedrizzetti | A61B 8/0883 382/128 |
| 2010/0020244 A1* | 1/2010 | Mitsuya | H04N 5/23248 348/699 |
| 2013/0034272 A1* | 2/2013 | Thomas | G06T 7/0016 382/107 |
| 2013/0116739 A1* | 5/2013 | Brada | A61B 6/486 607/9 |
| 2014/0334697 A1* | 11/2014 | Kersten | A61B 5/0816 382/128 |
| 2016/0180546 A1* | 6/2016 | Kim | G06T 7/251 382/103 |
| 2016/0210747 A1* | 7/2016 | Hay | G06F 16/7335 |
| 2016/0253820 A1* | 9/2016 | Jeanne | A61B 5/7207 382/107 |

OTHER PUBLICATIONS

Bruce D. Lucas & Takeo Kanade, "An Iterative Image Registration Technique with an Application to Stereo Vision," *Proceedings of Imaging Understanding Workshop* (1981), pp. 121-130.

Berthold K.P. Horn & Brian G. Schunck, "Determining Optical Flow," *Artificial Intelligence*, vol. 17 (1981), pp. 185-203.

Gunnar Farnebäck, "Two-Frame Motion Estimation Based on Polynomial Expansion," *Scandinavian Conference on Image Analysis* (2003), pp. 363-370.

Bernhard Schölkopf et al, "Kernel Principal Component Analysis," *International Conference on Artificial Neural Networks* (1997), pp. 583-588.

Geoffrey E. Hinton et al., "A Fast Learning Algorithm for Deep Belief Nets," *Neural Computation*, vol. 18 (2006), pp. 1527-1554.

* cited by examiner

METHOD, STORAGE MEDIUM, AND SYSTEM FOR ANALYZING IMAGE SEQUENCES OF PERIODIC PHYSIOLOGICAL ACTIVITIES

TECHNICAL FIELD

The invention relates to a method, non-transitory computer-readable storage medium, and system for performing analysis on image sequences, especially to a method, computer-readable storage medium, and system for performing analysis on image sequences of periodic physiological activities.

BACKGROUND

The periods of physiological activity, such as the respiratory and cardiac periods, have an important effect on synchronizing the image frames in the image sequences of the physiological activity. The phase of an individual frame in an image sequence of the periodic physiological activity provides critical intermediate information for medical imaging and diagnosis. For example, when the doctor interprets pulmonary CT image sequences, he/she needs to mark up the exhale phase and inhale phase. For another example, when reconstructing a 3D image for a physiological structure using 2D images acquired from various scanning angles, it is necessary for the 2D images to have the same phase in the periodic physiological activity. For another example, in the field of cardiovascular diagnosis and treatment, accurately determining the phase of individual frame in the cardiac period facilitates deriving other important physiological parameters, such as heart rate, cardiac period, etc.

Conventionally, separate periodic-monitoring devices are used, such as electrocardiograph, respiratory management system, etc., for recording and monitoring the related clinical information. For example, an ECG gating device is typically used to generate a synchronizing ECG gating signal, in order to correlate the image frames and their cardiac phases. However, these monitoring devices are not part of the standard configuration for most common imaging systems, and the additional devices occupy extra space at the imaging scene.

Extant methods for evaluating the cardiac periodic phase on the basis of image sequence of vessel generally include the following. One finds the time window with the slowest phase change by calculating the difference between different frames (e.g., adjacent frames) to perform the analysis using several image frames within the time window. This method does not evaluate the phase of each frame and cannot distinguish the diastole from the systole. In addition, this method is sensitive to background noise in the image. Another method is to determine the phase on the basis of comparison to a reference image. This method requires manual selection of the reference image at the desired phase or assumes a high similarity between a reference image in a database and the present image sequence. This method suffers from the same problems when used for image sequences for other periodic physiological activity other than the cardiac activity, such as pulmonary activity in the respiration period.

SUMMARY

Embodiments of the present disclosure solve a technical problem in extant methods for estimating periodic phases: the reliance on additional periodic-signal-monitoring devices and/or manually selected reference images, which increases the complexity of the system and workload of the clinicians. Eliminating the dependence on these additional devices and freeing the clinicians from manual work by enabling automatic analysis on image sequences of periodic physiological activities to obtain the phase of individual frames increases resource efficiency and allows a computer to perform previously manual functions.

Embodiments of the present disclosure further solve another technical problem in extant methods for evaluating cardiac periodic phases on the basis of image sequences: sensitivity to background noise in the images. For example, most extant methods cannot evaluate the phases of individual frame images in the periodic motion based on the temporal change of the image sequence itself with sufficient speed and accuracy and/or without manual intervention.

Embodiments of the present disclosure include a method and a system for efficiently estimating the phases of image frames based on the dynamic changes of image sequences of periodic physiological activity without additional monitoring devices or other reference images.

In one embodiment of the present disclosure, a computer-implemented method for analyzing an image sequence of a periodic physiological activity may comprise:

receiving the image sequence acquired by an imaging device, the image sequence having a plurality of frames;

determining local motions for pixels in each frame of the image sequence, wherein the local motion for a pixel is determined using corresponding pixels in frames adjacent to the frame to which the pixel belongs;

determining principal motions for the plurality of frames based on the local motions;

determining a motion magnitude profile based on the principal motions; and determining the phase of each frame in the image sequence based on the motion magnitude profile.

In one embodiment, determining the local motions may include calculating a local motion vector for each pixel.

In one embodiment, calculating a local motion vector for each pixel may comprise applying at least one of non-rigid matching, patch matching between adjacent frames, and optical flow estimation.

In one embodiment, determining the principal motions may include calculating a principal motion vector using a principal components analysis.

In one embodiment, the method may further comprise:

identifying a subset of the local motions caused by non-physiological activity; and excluding the subset from the principal components analysis.

In one embodiment, determining the motion magnitude profile may further include calculating global motion magnitudes for the plurality of frames; and integrating the global motion magnitudes.

In one embodiment, determining the phase of each frame may comprise determining a global displacement for the frame, and determines a corresponding position of the global displacement on the global motion magnitude profile.

In one embodiment, the periodic physiological activity may include a cardiac activity or a respiratory activity.

In one embodiment, determining the phase of each frame is based on a zero-crossing and a slope on the global motion magnitude profile.

In another embodiment of present disclosure, a non-transitory computer-readable storage medium may have computer-executable instructions stored thereon, wherein the instructions, when executed by a processor, cause the processor to perform a method for analyzing an image sequence of a periodic physiological activity, and the method may comprise:

receiving the image sequence acquired by an imaging device, the image sequence having a plurality of frames;

determining local motions for pixels in each frame of the image sequence, wherein the local motion for a pixel is determined using corresponding pixels in frames adjacent to the frame to which the pixel belongs;

determining principal motions for the plurality of frames based on the local motions;

determining a motion magnitude profile based on the principal motions; and determining the phase of each frame in the image sequence based on the motion magnitude profile In yet another embodiment of present disclosure, a system for performing analysis on an image sequence of periodic physiological activity may comprise:

a processor; and a memory storing computer-executable instructions that, when executed by the processor, may cause the processor to:
  receive the image sequence acquired by an imaging device, the image sequence having a plurality of frames;
  determine local motions for pixels in each frame of the image sequence, wherein the local motion for a pixel is determined using corresponding pixels in frames adjacent to the frame to which the pixel belongs;
  determine principal motions for the plurality of frames based on the local motions;
  determine a motion magnitude profile based on the principal motions; and
  determine the phase of each frame in the image sequence based on the motion magnitude profile.

In one embodiment, the instructions may further comprise:

marking the calculated phases on corresponding frames, and storing, in the memory, the frames marked with the phases.

In one embodiment, the memory may be in communication with a medical database storing at least one of the image sequence and the frames marked with the phases.

In one embodiment, the system may further comprise a display configured to display the frames marked with the phases.

Embodiments of the present disclosure may achieve the following technical advantages over, extant methods: 1) eliminating the need for manually selected reference images and/or for additional monitoring devices, 2) reducing sensitivity to image background noise compared to extant methods and also reducing sensitivity to interfering physiological activities. Embodiments of the present disclosure may be more responsive to dynamic changes of the image sequence and thus more accurately reflect the dynamic process depicted in the image sequence compared with extant methods. Furthermore, embodiments of the present disclosure may be performed automatically (i.e., without manual intervention) and more quickly than extant methods (e.g., with an execution time within a clinically acceptable range).

BRIEF DESCRIPTION OF THE DRAWINGS

Embodiments of the present invention are described in detail below with reference to the accompanying drawings, which are not to be construed as limiting but as exemplary. The features, advantages, and techniques and applicability of the exemplary embodiments are described below with reference to the accompanying drawings in which like reference numerals refer to like elements and in the drawings.

DETAILED DESCRIPTION

Figure 1:
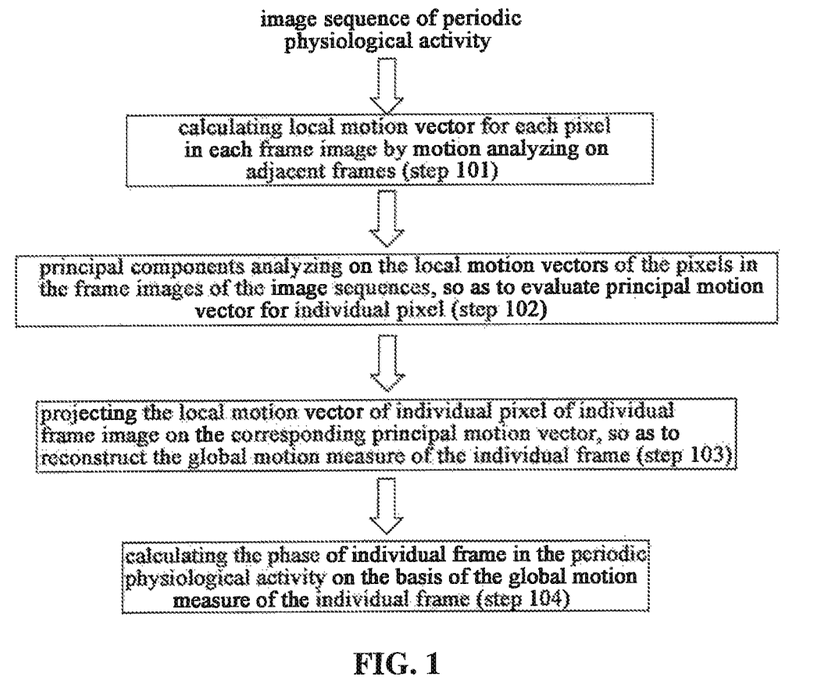
FIG. 1 illustrates a method for performing analysis on an image sequence of periodic physiological activity, according to an exemplary embodiment of present disclosure.

As illustrated in FIG. 1, using an image sequence of a periodic physiological activity having a plurality of frames, a method of present disclosure includes calculating a local motion vector for each pixel in each frame by applying motion estimation on adjacent frames (step 101, also referred to as the adjacent frames motion analysis step); applying principal components analysis on the local motion vectors to evaluate a principal motion vector for each pixel (step 102, also referred to as the principal components analysis step); projecting the local motion vectors onto the corresponding principal motion vectors to reconstruct a global motion magnitude for each frame (step 103, also referred to as the global motion magnitude reconstruction step); in some embodiments, reconstructing the global motion magnitudes may include reconstructing the motion magnitude curve of the periodic physiological activity; and calculating the phase of each frame based on the global motion magnitudes (step 104, also referred to as the phase calculating step).

Exemplary embodiments of the above steps are described and explained below.

Adjacent Frames Motion Analysis

Various methods may be used to calculate the local motion vector of each pixel by comparing the corresponding pixel in a previous frame with that of a latter frame. For example, a non-rigid matching method may be used. Such methods find the match of each pixel between different frames of a sequence (or between regions of interests of the different frames), and calculate the local motion vector of each pixel by calculating the displacement between the matching pixels. Non-rigid matching methods, in order to calculate an optimal match, need to solve a relatively complicated global optimization problem, and usually require a relatively accurate evaluation of initial parameters. Thus, it is relatively complicated and generally computationally expensive.

In another example, patch matching between adjacent frames may be used to calculate the local motion vectors. For instance, such methods may be implemented as follows: setting an independent patch in the previous frame and determining its location in the previous frame, such as (u, v); selecting patches with the same size as that of the independent patch in the latter frame within a searching region (such as (u+Δu, v+Δv)) defined with respect to the location of the independent patch in the previous frame; calculating the convolutions of the selected patches and the independent patch as correlation coefficients; using the patch with the largest correlation coefficient as the matching patch for the independent patch; and calculating the difference between the matching patch and the independent patch as the local motion vector of the center pixel in the independent patch. By moving the independent patch centered on an individual pixel, the local motion vector of each pixel between two adjacent frames can be obtained.

In one embodiment, the local motion vector of each pixel between adjacent two frames may be calculated using an optical flow method. For evaluating the cardiac phase, the optical flow method is generally efficient and does not require an accurate evaluation of initial parameters.

Optical flow generally refers to the motion pattern of objects in a visual scene caused by the relative motion between an observer and a scene. It may be caused by the motion of the foreground subject itself, the motion of the camera, or both. An optical flow field generally refers to a 2D instant speed field for all pixels in an image, where the 2D speed vectors of the field are projections of a 3D speed vector of a visual point in the scenery on the imaging surface. Therefore, optical flow includes motion information regarding the observed object, as well as information regarding the 3D structure of the scenery. Optical flow estimation generally refers to a method of calculating a corresponding relation between a previous frame and a current frame using changes of pixels in an image sequence in the temporal domain and correlations between adjacent frames in order to calculate motion information of the object between adjacent frames.

Assuming, in a group of time-sequent images, a location of a feature point at the $t^{th}$ frame is represented as $(x^t, y^t)$, then the location of this feature point at the $t+1^{th}$ frame may be represented as $(x^{t+1}, y^{t+1})$, and the motion vector of this point between the two frames may be represented as $(u^t, v^t)=(x^{t+1}, y^{t+1})-(x^t, y^t)$. There are many extant optical flow estimation methods, e.g., the Lucas-Kanade algorithm based on patch matching, the Horn-Schunck algorithm based on smooth constraint on the optical flow field, and the Farneback algorithm for evaluating dense optical flow. One of ordinary skill may adapt different local motion estimation methods for use in embodiments of the present disclosure. Accordingly, systems and methods of the present disclosure are not limited to the non-rigid matching method, image patch convolution matching method, and the optical flow estimation methods disclosed above.

For coronary X-ray angiography application, the Farneback algorithm may be used. This method may be adapted to calculate relatively large motions between two frames and has a relatively fast computation speed. Since the main visual objects in this exemplary application are the vessels filled with the contrast agent, the motion mainly comprises motion of the vessel and its surroundings, as shown in FIG. 2.

Figure 2:
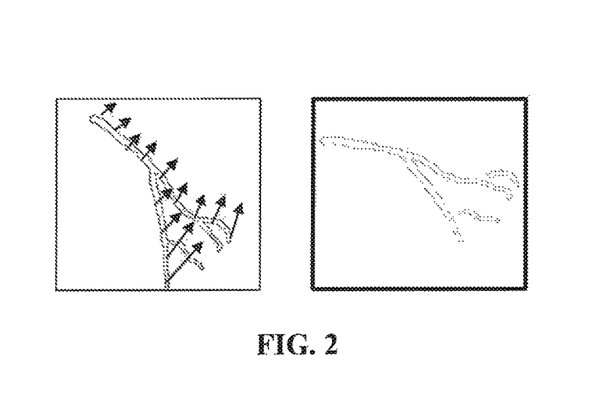
FIG. 2 illustrates a schematic diagram of calculating the local motion vector field of individual pixels between adjacent frames using an optical flow estimation method, according to an exemplary embodiment of present disclosure.

FIG. 2 illustrates a schematic diagram of an example of calculating the local motion vector field of individual pixels between adjacent frames using an optical flow estimation method according to an embodiment of present invention. Particularly, FIG. 2 depicts two successive frames of X-ray images, and the arrowheads schematically show the optical flow detected from the two frames, that is, the local motion vectors of the individual pixels.

Principal Motion Analysis

After the local motion vectors of the pixels are calculated, principal components analysis (PCA) may be used to extract the principal motion vector of the image sequence. The global motion magnitudes of each frame, which characterize the global temporal changes of the image sequence of the periodic physiological activity, may then be calculated from the principal motion vectors.

A cardiovascular X-ray image sequence is used as an example in the following description, but the PCA method may be applied to any image sequence. In a cardiovascular X-ray image sequence, the coronary artery is generally the main moving object. Under normal image acquisition conditions, the motion and/or the deformation of the vessels in the image sequence are typically caused by cardiac motion (with some background respiratory motion); therefore, the generated first principal component usually corresponds to the cardiac motion.

In one example, we use $F^t$ to represent the optical flow field of the $t^{th}$ frame, which is a collection of the optical flow vectors of the pixels in this frame. $F^t=\{(u_{ij}^t, v_{ij}^t), i=1, \ldots, H, j=1, \ldots, W\}$, where H and W are the height and width of the 2D frame image (e.g., the pixel numbers of the image in the y direction and x direction), respectively. In some embodiments, the elements in $F^t$ may be extended in sequence into a one-dimension vector with a length of 2HW, referred to as $EF^t$, for example, $EF^t=(u_{00}^t, v_{00}^t, u_{01}^t, v_{01}^t, \ldots, u_{0W}^t, v_{0W}^t, u_{10}^t, v_{10}^t, u_{11}^t, v_{11}^t, \ldots)$.

The one-dimension vectors EF of N frames of the image sequence may be combined to obtain a high-dimension motion vector, which is represented as $D=\{EF^t, t=1, \ldots, N\}$, with N as the frame number. D may be a (2HW)×N matrix. Accordingly, using PCA, the eigenvector corresponding to the largest eigenvalue of this high-dimension motion vector, which is also referred as the first principal component or the principal motion vector is and represented as $X^*$, may be obtained.

$$X^* = \arg\max_{\|x\|=1} \operatorname{var}(D^T X) \qquad \text{Formula 1}$$

This principal motion vector X* characterizes the direction and magnitude of the temporal motion of individual pixel (also referred to as the principal motion direction and magnitude).

Using PCA, the influence of at least some background noise, especially static noise, may be filtered out. Compared to extant methods which only calculate the image differences between different frames or differences with respect to reference images, PCA is more robust to influence from background noise.

In embodiments where the image acquisition is of poor quality, with relatively high-varying background noise, prior to calculating the local motion vector of each pixel, a denoising pre-processing may be performed. For example, the frame may be segmented in order to obtain the local motion vectors of the pixels corresponding to the target and the pixels corresponding to the background. Thereafter, the location motion vectors of the background may be subtracted from the local motion vectors of the target to obtain the local motion vectors of the pixels of the target excluding the influence from the background, e.g., caused by background noise. In one embodiment, PCA is applied directly to the images with adequate quality and low background noise, e.g., a cardiovascular image sequence, a pulmonary CT image sequence, etc. For images with relatively strong background noises and/or imaging artifacts, an ultrasonic image sequence, etc., denoising pre-processing may be performed before PCA.

The principal motion analysis may incorporate various methods, including linear decomposition, non-linear decomposition, etc. For example, in embodiments where the image sequence is one of coronary angiography, under a condition of normal temporal sampling rate (e.g., a rate of 15 frames per second), the principal motion component may be obtained by applying PCA with linear decomposition. Accordingly linear decomposition may be used to implement the principal component analysis. Linear decomposition has a higher calculation speed and consumes less resources compared to non-linear decomposition.

For example, PCA may incorporate linear matrix decomposition, for example, singular value decomposition (SVD) or eigenvalue decomposition (EVD).

For instance, in singular value decomposition, matrix D may be decomposed as:

$$D=USV^T, \qquad \text{Formula 2}$$

where U and V are orthogonal matrixes, and S is a diagonal matrix. In this example, the principal component (also referred to as the principal motion vector) X* is equal to a first column vector of V.

In other embodiments where the mixing of different motions cannot be approximated in a linear manner, non-linear decomposition may be incorporated, e.g., kernel PCA, deep belief network, or the like.

In one embodiment, after calculating the local motion vector of each pixel and before applying PCA to extract the principal motion vectors, pre-processing may be performed on the local motion vectors in order to identify the local motion vectors caused by specific motion of non-physiological activity. For example, the imaging device acquisition console may be moved during image acquisition in order to observe the vessel more clearly, and this may result in a step-like magnitude change of the local motion vectors in the frames during moving period. For example, if this step-like change occurs in the local motion vectors of the pixels in the $20^{th}$ to $30^{th}$ frames, it may be caused by the image device acquisition console moving at a constant speed then stopping.

Figure 3A:
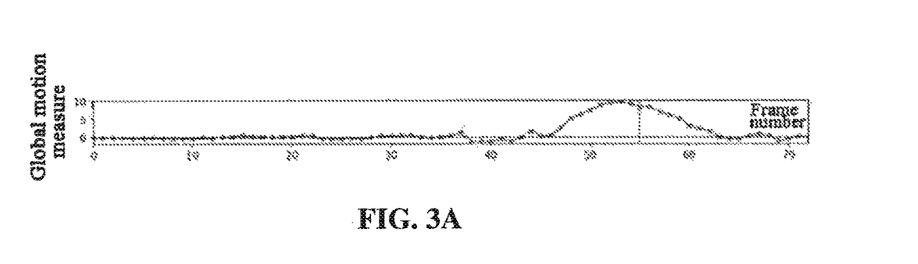
FIG. 3A shows an exemplary profile of the global motion magnitude of the pixels in individual frames in the principal motion direction in an embodiment where a specific motion due to non-physiological activity occurs during the sequence imaging, with frame numbers as the lateral axis and the global motion magnitude as the longitudinal axis.
Figure 3B:
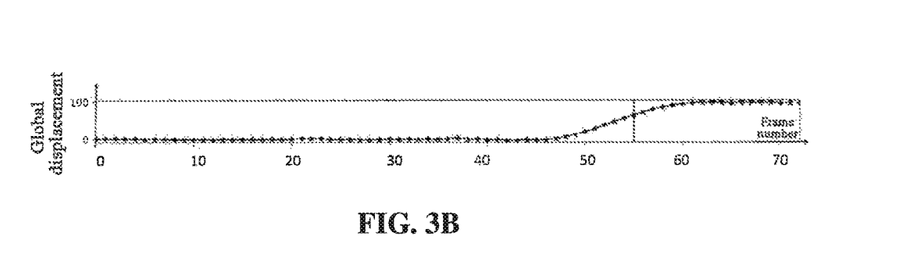
FIG. 3B shows an exemplary profile of the global displacement of the pixels in individual frames in the principal motion direction in the embodiment of FIG. 3A, with the frame number as the lateral axis and the global displacement as the longitudinal axis.

If such specific motion occurs in the image sequence, then the first principal component calculated using PCA on the local motion vectors usually no longer corresponds to the periodic cardiac motion. The motion and displacement in the principal motion direction of the individual frame image as further calculated is caused, to a large extent, by the movement of the imaging device, as shown in FIG. 3A and FIG. 3B. In this case, the cardiac phase evaluation will produce a result that is not accurate.

In one embodiment, after identifying the local motion vectors) caused by the non-physiological activity, a warning may be provided to the doctor to stop the consequent analysis upon a confirmation from the doctor or automatically. This may ensure that the to-be-analyzed image sequence is acquired under the condition that the imaging device does not move. For example, such identification may be implemented using the following sub-method: setting a threshold (e.g., empirically); when the magnitude of one or more local motion vectors exceeds the threshold, non-physiological activity is identified. Accordingly, PCA may be prevented from being performed on the local motion vectors into which motion information of non-physiological activity has been introduced and thus may not be used for the sequent phase analysis, avoiding waste of resources.

Global Motion Magnitude Reconstruction and Phase Evaluation

Using the local motion vector of each pixel of each frame calculated, e.g., using optical flow estimation, and the principal motion vector of the pixel corresponding to, for example, cardiac motion, the projection of the local motion vector of each pixel of each frame onto the principal motion direction characterized by its principal motion vector may be calculated in order to obtain a motion magnitude profile of the periodic motion corresponding to, for example, the cardiac activity. The global motion magnitude m(t) corresponding to each frame, for example, may be obtained by summing the projection coefficients of the local motion vector of each pixel in the frame projected onto the principal motion vector of the corresponding pixel.

$$m(t)=\text{dot}(X^*, X^t) \qquad \text{Formula 3}$$

In some embodiments, in order to exclude the influence of the magnitude of the principal motion vector upon projection, the projection coefficient may be divided by the Euclidean norm of the corresponding principal motion vector in order to obtain the global motion magnitude corresponding to each frame m(t), as shown in Formula 4.

$$m(t)=\text{dot}(X^*, X^t)/|X^*| \qquad \text{Formula 4}$$

Figure 4A:
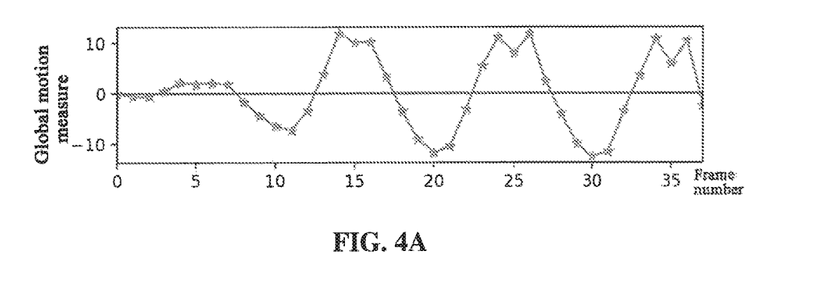
FIG. 4A shows an exemplary profile of the global motion magnitudes of a coronary angiography image sequence obtained according to an exemplary embodiment of present disclosure, with the frame numbers as the lateral axis and the global motion magnitudes as the longitudinal axis.

Accordingly, a profile of a global motion magnitude of, for example, the coronary angiography image sequence, as shown in the example of FIG. 4A, with the frame number as the x axis and the global motion magnitude as the y axis. Based on the global motion magnitude of the individual frame, the phase of the individual frame in the periodic physiological activity may be calculated.

Taking the cardiac cycle as an example, different cardiac phases correspond to different motion characteristics, as shown in Table 1.

TABLE 1

Motion descriptions of the cardiac phases

| Cardiac phase | Corresponding characteristics of the global motion magnitude |
| --- | --- |
| isovolumic contraction period | contraction motion with relatively lower speed |
| rapid ejection period | rapid contraction motion |
| reduced ejection period | continue contraction motion with speed reduced |
| isovolumic relaxation period | transform from contraction motion into relaxation motion |
| rapid filling period | rapid relaxation motion |
| slow filing period | continue relaxation motion with speed reduced |
| atrial systole period | transform from relaxation motion into contraction motion |

In the example of FIG. 4A, a positive global motion magnitude on the y axis represents a relaxation period while a negative global motion magnitude represents a contraction motion. The magnitude of the global motion represents the instant speed of the motion. For example, the zero-crossing with a positive slope signifies that the cardiac motion is transforming from a contraction motion into a relaxation motion, with a ventricular end systolic period nearby; on the other hand, the zero-crossing with a negative slope signifies that the cardiac motion is transforming from the relaxation motion into the contraction motion, with a ventricular end diastolic period nearby. In one embodiment, upon the determination of the ventricular end systolic period and ventricular end diastolic period, an interval of a complete cardiac period may be defined. The cardiac phase corresponding to the individual frame, as well as the corresponding physical phase in the interval of 0~2π, may be determined based on the distribution ratio of each phase in the cardiac period.

Figure 4B:
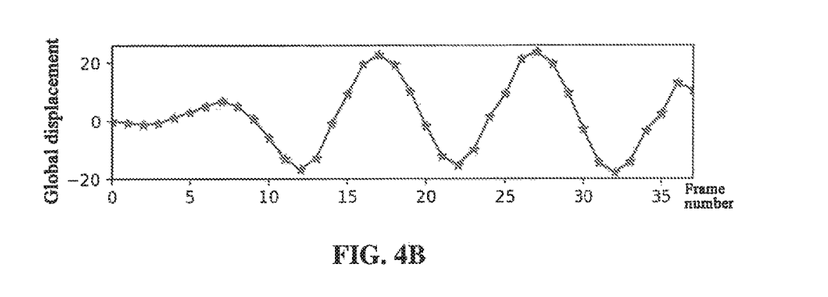
FIG. 4B shows an exemplary profile of the global displacement magnitudes of a coronary angiography image sequence obtained according to another exemplary embodiment of present disclosure, with the frame number as the lateral axis and the global displacement magnitudes as the longitudinal axis.

To further improve the evaluation accuracy of, e.g., the cardiac phases, in some embodiments, the global motion magnitude m(x) may be integrated over time (see Formula 5) in order to obtain the profile of the global displacement d(t) of the individual frame, as shown in the example of FIG. 4B.

$$d(t)=\int_0^t m(x)dx \qquad \text{Formula 5}$$

FIG. 4B shows an example profile of the global displacement of the image sequence obtained according to an embodiment of the present disclosure, with the frame number as the lateral axis and the magnitude of the global displacement as the longitudinal axis. From the displacement profile, the period of the motion may be evaluated and the cardiac phase corresponding to each frame discerned. For example, in FIG. 4B, in addition to the slope and zero-crossing discussed above, the peak corresponds to the cardiac end diastolic period while the valley corresponds to the cardiac end systolic period. In some embodiments, upon the determination of the ventricular end systolic (and/or diastolic) period and/or upon the determination of the adjacent ventricular end systolic (and/or diastolic) period, the interval of a complete cardiac period may be defined. Based on the distribution ratio of individual phases in the cardiac period, the cardiac phase corresponding to the individual frame, as well as the corresponding physical phase in the interval of 0~2π, may be determined.

Figure 5:
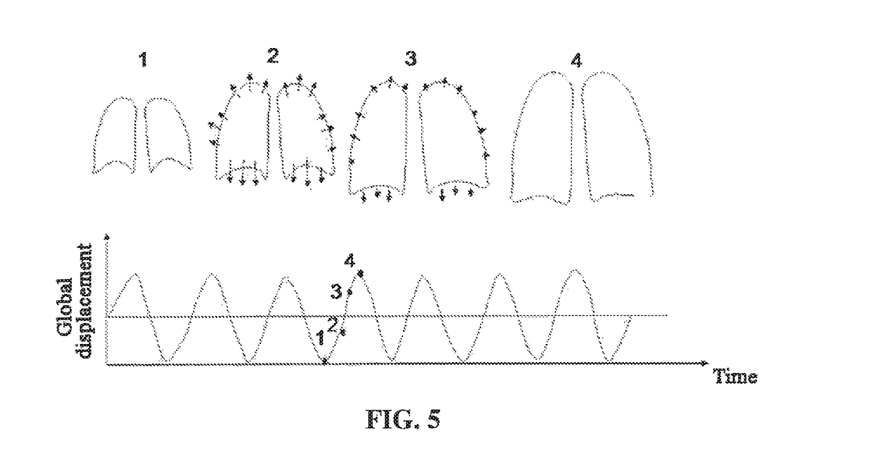
FIG. 5 shows an exemplary profile of global displacements of a pulmonary 4D CT image sequence obtained according to a further exemplary embodiment of present disclosure, wherein reference numbers 1, 2, 3, and 4 identify the four phases of lung dilatation, respectively, with the status of the lung during the lung dilatation at the four phases identified by reference numbers 1, 2, 3, and 4, respectively.

Embodiments of the present disclosure are not limited to the clinical application of coronary angiography but may also be applied to analysis on periodic temporal image sequences in other technical fields, such as computer vision. For example, analyzing processes of the present disclosure may be applied to a pulmonary 4D CT image sequence of the periodic respiratory activity. FIG. 5 shows an example profile of the global displacement obtained from a pulmonary 4D CT image sequence, where reference numbers 1, 2, 3, and 4 are used to identify the four phases during the lung dilatation, respectively, and shows the status of the lung during the lung dilatation at the four phases identified by reference numbers 1, 2, 3, and 4, respectively.

By determining the peaks and valleys in the profile of the global displacement, phases 4 and 1 may be obtained. In addition, phases 3 and 2 may be obtained by proportional extrapolation in the interval between phase 4 and phase 1.

Figure 6:
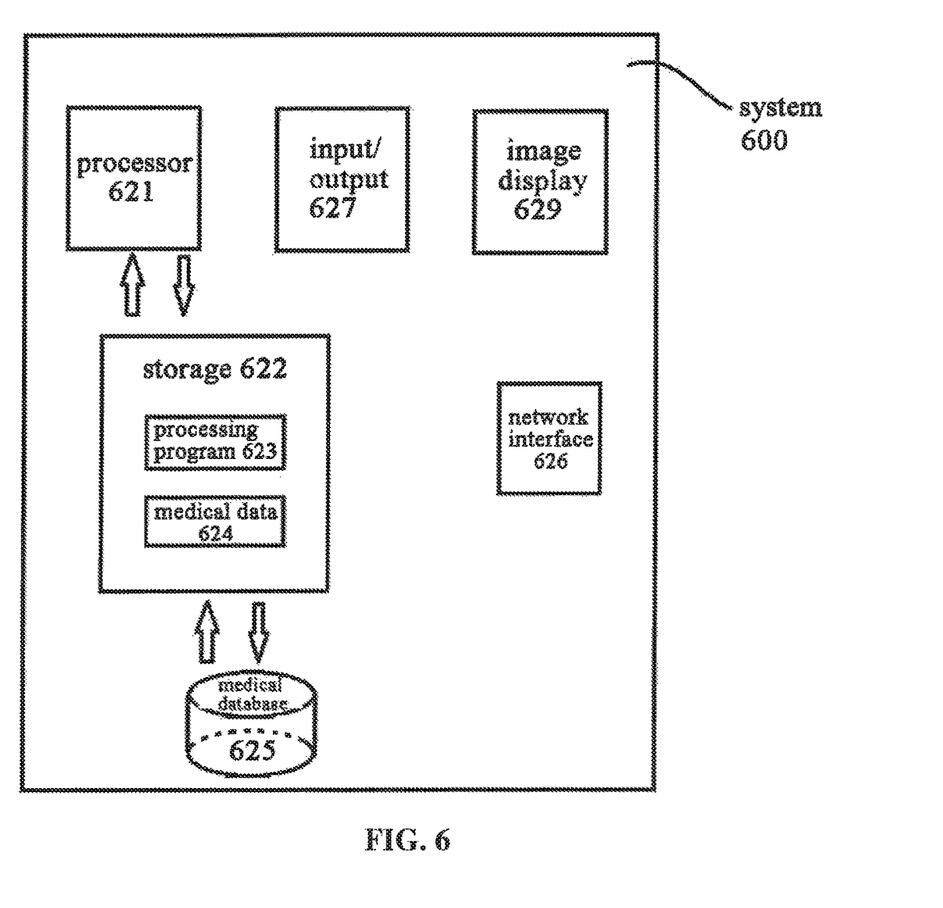
FIG. 6 illustrates an exemplary system for performing analysis on an image sequence of periodic physiological activity, according to an exemplary embodiment of present disclosure.

FIG. 6 is an illustration of an example system for performing analysis on an image sequence of a periodic physiological activity according to an embodiment of the present disclosure. As will be appreciated by those skilled in the art, in some embodiments, system 600 may be a specialized computer or a general purpose computer. For example, system 600 may be a computer customized for a hospital for processing image data acquisition and image data processing tasks, or may be a server located in the cloud. In another example, system 600 may be integrated into an imaging device for acquiring image sequences for the patient, e.g., a DSA imaging device, a pulmonary CT imaging device, etc.

System 600 may include a processor 621 and a memory 622. In some embodiments, as shown in FIG. 6, system 600 may additionally include at least one of a medical database 625, an input/output 627, a network interface 626, and an image display 629.

Processor 621 may be a processing device that includes one or more general processing devices, such as a microprocessor, a central processing unit (CPU), a graphics processing unit (GPU), and the like. More specifically, processor 621 may be a complex instruction set computer (CISC) microprocessor, a reduced instruction set computer (RISC) microprocessor, a very long instruction word (VLIW) microprocessor, a processor executing other instruction sets, or a processor that executes a combination of instruction sets. Processor 621 may also be one or more dedicated processing devices, such as application specific integrated circuits (ASICs), field programmable gate arrays (FPGAs), digital signal processors (DSPs), system-on-a-chip (SoC), and the like.

Processor 621 may be communicatively coupled to the memory 622 and configured to execute computer-executable instructions stored therein. Memory 622 may include a read-only memory (ROM), a flash memory, a random access memory (RAM), a static memory, etc. In some embodiments, memory 622 may store computer-executable instructions of one or more processing programs 623 and/or data generated when a computer program is executed. Processor 621 may execute processing program 623 to implement methods for performing analysis on an image sequence of a periodic physiological activity disclosed herein, including the example described in conjunction with FIG. 1. Optionally, when executing processing program 623, processor 621 may further execute methods for calculating the local motion vector of the individual pixel between adjacent frames as described above, e.g., the example for calculating the local motion vector of the individual pixel between adjacent frames using the optical flow estimation method described in conjunction with FIG. 2. Optionally, when executing processing program 623, processor 621 may further execute methods of extracting the principal motion vector of each pixel of each frame of the image sequence of the periodic physiological activity using PCA as described above. Optionally, when executing processing program 623, processor 621 may further execute the phase evaluation described in conjunction with FIG. 4A, FIG. 4B, and FIG.

5, including projecting the local motion vector of each pixel of the frame onto the corresponding principal motion vector in order to obtain the global motion magnitude curve, determining the global displacement on the basis of the global motion magnitudes, and determining the phase of each frame on the basis of the global displacement. Optionally, when executing processing program 623, processor 621 may perform pre-processing (e.g., identifying a non-physiological activity, denoising, etc.) on the local motion vectors as described in conjunction with FIG. 3A and FIG. 3B.

Processor 621 may also send and/or receive medical data 624 to and/or from memory 622. For example, processor 621 may receive the image sequence of the periodic physiological activity stored in memory 622. In some embodiments, when executing processing program 623, processor 621 may mark the evaluated phase onto the corresponding image frame and transmit the image frames marked with the phases into memory 622. Optionally, memory 622 is able to communicate with medical database 625 to obtain image sequences therefrom and/or to transmit the image frames marked with phases to medical database 625 to be acquired and used by users authorized to access medical database 625.

Medical database 625 is optional and may include multiple devices positioned in a centralized or a distributed manner. Processor 621 may communicate with medical database 625 to read the image sequence into memory 622 and/or store the image sequence from memory 622 to medical database 625. Alternatively, medical database 625 may store image sequences to be evaluated. Processor 621 may communicate with the medical database 625, transmit and store the images marked with the phases into memory 622 and display them on the image display 629 to be labeled by a physician, e.g., using professional software and the input/output 627 and/or to be constructed as the dataset for 3D reconstruction by activating (one or more) processing program(s). For example, the 3D reconstruction may group the 2D images in accordance with the phases, such that the 2D images in the same group have the same phase and/or approximate but different projection angles, and the groups of the 2D images may then be used for 3D reconstruction.

The input/output 627 may be configured to allow system 600 to receive and/or send data. The input/output 627 may include one or more digital and/or analog communication devices that allow system 600 to communicate with a user and/or other machines and devices. For example, the input/output 627 may include a keyboard and a mouse that allow the user to provide input.

The network interface 626 may include a network adapter, a cable connector, a serial connector, a USB connector, a parallel connector, a high speed data transmission adapter such as optical fiber, USB 3.0, lightning, a wireless network adapter (such as a WiFi adapter, a telecommunication (3G, 4G/LTE, etc.) adapter, etc.), or the like. System 600 may be connected to the network through the network interface 626.

Besides displaying the medical images, image display 629 may also display other information, such as the phase of the image, a warning for the doctor upon identifying non-physiological activity, etc. For example, image display 629 may be an LCD, a CRT, an LED display, or the like.

Various operations or functions are described herein, which may be implemented as software code or instructions or defined as software code or instructions. Such content may be source code or differential code ("delta" or "patch" code) that can be executed directly ("object" or "executable" form). The software implementation of the embodiments described herein may be provided via an article of manufacture storing code or instructions therein and/or via a method in which a communication interface is operated to send data via the communication interface. The Machine- or computer-readable storage medium may cause the machine to perform the described functions or operations and may include any mechanism for storing information in a form accessible by a machine (e.g., computing device, electronic system, etc.), such as recordable/non-recordable media (e.g., read-only memory (RUM), random access memory (RAM), disk storage media, optical storage media, flash memory devices, etc.). The communication interface may include any mechanism that interfaces with any of the wired media, wireless media, optical media, or the like, to communicate with another device, such as a memory bus interface, a processor bus interface, an Internet connection, a disk controller, and the like. By providing configuration parameters and/or sending a signal, the communication interface may be configured to prepare the communication interface to provide a data signal describing the software content. The communication interface may be accessed via one or more commands or signals sent to the communication interface.

The present disclosure also relates to a system for performing the operations herein. The system may be constructed specifically for the intended purpose or the system may include a computer that is selectively activated or configured by a computer program stored in the computer. Such a computer program may be stored in a computer readable storage medium such as, but not limited to, any type of disk including a floppy disk, an optical disk, a CDROM, a magneto-optical disk, a read-only memory (ROM), a random access memory (RAM), an EPROM, an EEPROM, a magnetic card, an optical card, or any type of medium suitable for storing electronic instructions, wherein each medium is coupled to a computer system bus.

It is intended that the specification and examples be considered as exemplary only, with a true scope being indicated by the following claims and their equivalents.

What is claimed is:

1. A computer-implemented method for analyzing an image sequence of a periodic physiological activity, the method comprising:
   receiving the image sequence acquired by an imaging device, the image sequence having a plurality of frames;
   determining local motions for pixels in each frame of the image sequence, wherein the local motion for a pixel is determined using corresponding pixels in frames adjacent to the frame to which the pixel belongs;
   determining principal motions for the plurality of frames based on the local motions;
   determining a motion magnitude profile based on the principal motions; and
   determining the phase of each frame in the image sequence based on the motion magnitude profile.

2. The method of claim 1, wherein determining the local motions includes calculating a local motion vector for each pixel.

3. The method of claim 2, wherein calculating a local motion vector for each pixel comprises applying at least one of non-rigid matching, patch matching between adjacent frames, and optical flow estimation.

4. The method of claim 1, wherein determining the principal motions includes' calculating a principal motion vector using a principal components analysis.

5. The method of claim 4, further comprising:
identifying a subset of the local motions caused by non-physiological activity; and
excluding the subset from the principal components analysis.

6. The method of claim 1, wherein determining the motion magnitude profile further includes calculating global motion magnitudes for the plurality of frames; and integrating the global motion magnitudes.

7. The method of claim 6, wherein determining the phase of each frame comprises determining a global displacement for the frame, and determines a corresponding position of the global displacement on the global motion magnitude profile.

8. The method of claim 1, wherein the periodic physiological activity includes a cardiac activity or a respiratory activity.

9. The method of claim 6, wherein determining the phase of each frame is based on a zero-crossing and a slope on the global motion magnitude profile.

10. A non-transitory computer-readable storage medium, with computer-executable instructions stored thereon, wherein the instructions, when executed by a processor, cause the processor to perform a method for analyzing an image sequence of a periodic physiological activity, the method comprising:
receiving the image sequence acquired by an imaging device, the image sequence having a plurality of frames;
determining local motions for pixels in each frame of the image sequence, wherein the local motion for a pixel is determined using corresponding pixels in frames adjacent to the frame to which the pixel belongs;
determining principal motions for the plurality of frames based on the local motions;
determining a motion magnitude profile based on the principal motions; and
determining the phase of each frame in the image sequence based on the motion magnitude profile.

11. A system for performing analysis on an image sequence of periodic physiological activity, comprising:
a processor; and
a memory storing computer-executable instructions that, when executed by the processor, cause the processor to:
receive the image sequence acquired by an imaging device, the image sequence having a plurality of frames;
determine local motions for pixels in each frame of the image sequence, wherein the local motion for a pixel is determined using corresponding pixels in frames adjacent to the frame to which the pixel belongs;
determine principal motions for the plurality of frames based on the local motions;
determine a motion magnitude profile based on the principal motions; and
determine the phase of each frame in the image sequence based on the motion magnitude profile.

12. The system of claim 11, wherein the instructions further comprise:
marking the calculated phases on corresponding frames, and
storing, in the memory, the frames marked with the phases.

13. The system of claim 12, wherein the memory is in communication with a medical database storing at least one of the image sequence and the frames marked with the phases.

14. The system of claim 12, further comprising:
a display configured to display the frames marked with the phases.

* * * * *